(12) United States Patent
Tesson et al.

(10) Patent No.: US 9,533,960 B2
(45) Date of Patent: Jan. 3, 2017

(54) PREPARATION PROCESS OF CARBOXYLIC ACID DERIVATIVES AND INTERMEDIATES THEREOF

(71) Applicant: KERN PHARMA, S.L., Terrassa (ES)

(72) Inventors: Nicolas Tesson, L'hospitalet de Llobregat (ES); Montserrat Trilla Castaño, Barcelona (ES)

(73) Assignee: KERN PHARMA, S.L., Terrassa (ES)

( * ) Notice: Subject to any disclaimer, the term of this patent is extended or adjusted under 35 U.S.C. 154(b) by 0 days.

(21) Appl. No.: 14/410,517

(22) PCT Filed: Jun. 28, 2013

(86) PCT No.: PCT/EP2013/063649
§ 371 (c)(1),
(2) Date: Dec. 22, 2014

(87) PCT Pub. No.: WO2014/001511
PCT Pub. Date: Jan. 3, 2014

(65) Prior Publication Data
US 2015/0299140 A1    Oct. 22, 2015

(30) Foreign Application Priority Data
Jun. 29, 2012  (EP) .................................... 12382259

(51) Int. Cl.
| C07C 51/43 | (2006.01) |
| C07C 229/04 | (2006.01) |
| C07C 63/331 | (2006.01) |
| C07C 59/64 | (2006.01) |
| C07D 239/62 | (2006.01) |

(Continued)

(52) U.S. Cl.
CPC ............ *C07D 239/62* (2013.01); *C07C 51/412* (2013.01); *C07C 51/43* (2013.01); *C07C 59/64* (2013.01); *C07C 63/331* (2013.01); *C07C 229/04* (2013.01); *C07D 239/34* (2013.01)

(58) Field of Classification Search
CPC ...... C07C 52/43; C07C 51/412; C07C 229/04; C07C 63/331; C07C 59/64; C07C 239/34; C07C 239/62
See application file for complete search history.

(56) References Cited

U.S. PATENT DOCUMENTS

| 5,932,730 A | 8/1999 | Riechers et al. |
| 6,559,338 B1 | 5/2003 | Bernard et al. |

FOREIGN PATENT DOCUMENTS

| WO | WO2010070658 | 6/2010 |
| WO | WO2011004402 | 1/2011 |
| WO | WO2012017441 | 2/2012 |

OTHER PUBLICATIONS

Qiao et al., International Journal of Pharmaceutics, 419, 2011, 1-11.*

(Continued)

*Primary Examiner* — Sun Jae Yoo
(74) *Attorney, Agent, or Firm* — Squire Patton Boggs (US) LLP

(57) ABSTRACT

A cocrystal of (S)-2-hydroxy-3-methoxy-3,3-diphenylpropanoic acid and an amino acid, in particular L-valine or L-2-aminobutyric acid, their preparation processes, as well as the preparation process of Ambrisentan or Darusentan using any of the cocrystals of the invention.

11 Claims, 2 Drawing Sheets

(51) Int. Cl.
*C07D 239/34* (2006.01)
*C07C 51/41* (2006.01)

(56) References Cited

OTHER PUBLICATIONS

Karamertzanis, 2009, abstract, http://discovery.ucl.ac.uk/126551/.*
Chawla et al., CRIPS vol. 5 No. 1, 2004, pp. 9-12.*
Newman et al., DDT, vol. 8, No. 9, 2003, 898-905.*
International Search Report and Written Opinion for PCT/EP2013/063649.
Knopp et al., "Structural Similarity and its Suprises: Endothelin Receptor Antagonists-Progress Research and Development Report", *Organic Process Research & Development*, 2001, vol. 5, pp. 16-22.

* cited by examiner

PREPARATION PROCESS OF CARBOXYLIC ACID DERIVATIVES AND INTERMEDIATES THEREOF

The present invention relates to a process for preparing some carboxylic acid derivatives through the resolution of 2-hydroxy-3-methoxy-3,3-diphenylpropanoic acid, as for example Ambrisentan or Darusentan. It also relates to new cocrystals useful in such preparation process.

BACKGROUND ART

Ambrisentan is the International Nonproprietary Name (INN) of name (2S)-2-[(4,6-dimethylpyrimidin-2-yl)oxy]-3-methoxy-3,3-diphenylpropanoic acid, and has the CAS Nr 177036-94-1. It functions as an endothelin receptor antagonist, and is selective for the type A endothelin receptor ($ET_A$). It is a drug indicated for use in the treatment of pulmonary hypertension.

The structure of Ambrisentan corresponds to formula (I):

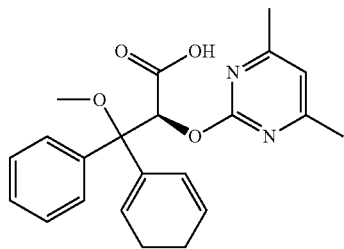

(I)

Different processes for the preparation of Ambrisentan and its salts are known in the art.

Ambrisentan was first described in the patent family of U.S. Pat. No. 5,932,730-BASF. In this patent it is disclosed a resolution step on a laboratory scale of 2-hydroxy-3-methoxy-3,3-diphenylpropanoic acid using as resolving agents either L-prolinemethylester (cf. Example 10) or (S)-1-(4-nitrophenyl)ethylamine (cf. Example 11). In the first case the diastereoisomeric salt of the (R)-2-hydroxy-3-methoxy-3,3-diphenylpropanoic acid is crystallized and separated off, and then from the mother liquor is subsequently isolated the (S)-2-hydroxy-3-methoxy-3,3-diphenylpropanoic acid (35% yield from racemic—100% ee). In the second case, the corresponding diastereoisomeric salt is crystallized from methyl tert-butyl ether/acetone, and subsequently it is converted into the free acid (35% yield from racemic—99.8% ee).

Unfortunately, these resolution agents are extremely expensive and would not be preferable for large scale production. In addition, the methyl prolinate could not be completely recycled since free methyl prolinate tends to form diketopiperazines (cf. eg. R. Jansen et al., *Organic Process Research & Development*, 2001, vol. 5, pp. 16-22). On the other hand, in U.S. Pat. No. 6,559,338 from the same applicant it is stated that when this described reaction was scaled up, additional working steps became necessary in order to ensure a high optical purity as the diastereoisomeric salt with (S)-1-(4-nitrophenyl)ethylamine crystallized with difficulty and could not be filtered off readily. As a consequence, some of the mother liquor remained in the crystals together with the enantiomer to be separated off. Only when the crystals were additionally stirred in the tank together with fresh solvent, and when the crystals which had been filtered off once more had been copiously rewashed, could the required optical purity be obtained.

U.S. Pat. No. 6,559,338 describes a process of resolution of 2-hydroxy-3-methoxy-3,3-diphenylpropanoic acid by using an optically active base (S)-1-(4-chlorophenyl)ethylamine. In Example 1, the resolution process is carried out using tert-butylmethylether/methanol as solvents and one of the diastereomeric salts formed is separated off with a yield of 36% and an ee >99.5%. The filtration problem is reported to be resolved with this agent. However, this resolving agent is also very expensive and would not be preferable for large-scale production.

Other resolution processes have also been disclosed in the art. Thus, WO2012017441A1-NATCO Pharma Ltd discloses an improved process of resolution of 2-hydroxy-3-methoxy-3,3-diphenylpropanoic acid with (S)-1-(4-nitrophenyl)ethylamine (as U.S. Pat. No. 5,932,730). According to the Example, it is obtained a compound having a chemical purity of 99.97% and a chiral purity of 99.98% with a yield of 27.5% in this step of the global process.

WO2011004402A2-Cadila Healthcare Limited describes a process of resolution of the 2-hydroxy-3-methoxy-3,3-diphenylpropanoic acid by using a chiral amine, in particular, (S)-3-methoxyphenylethylamine or (R)-2,4-dichlorophenylethylamine, and the diastereoisomeric salts thus obtained can be used in the following step of alkylation to form Ambrisentan. According to the Examples, in the alkylation step N,N-dimethylformamide is used as solvent, which implies that the recovery of the chiral amine most probably will be difficult to carry out.

Finally, WO2010070658A2-MSN Laboratories Ltd also discloses a process for the preparation of (S)-2-hydroxy-3-methoxy-3,3-diphenylpropanoic acid, which comprises treating the racemic 2-hydroxy-3-methoxy-3,3-diphenylpropanoic acid compound with R(+)-phenyl ethyl amine in a chlorinated solvent to provide the R(+)-phenyl ethyl amine salt of (S)-2-hydroxy-3-methoxy-3,3-diphenylpropanoic acid. In Example 22 is exemplified the process which uses chloroform as solvent. The use of chlorinated solvents and, specially, chloroform are not convenient in the industry.

The (S)-2-hydroxy-3-methoxy-3,3-diphenylpropanoic acid is an intermediate useful not only to prepare Ambrisentan but also to prepare other endothelin receptor antagonists such as Darusentan, which is the compound (2S)-2-(4,6-dimethoxypyrimidin-2-yl)oxy-3-methoxy-3,3-di(phenyl) propanoic acid. From what is known in the art is derived that there is still a need of a new resolution process for 2-hydroxy-3-methoxy-3,3-diphenylpropanoic acid using cheaper chiral agents and safer solvents.

SUMMARY OF THE INVENTION

Inventors have found a new resolution process for 2-hydroxy-3-methoxy-3,3-diphenylpropanoic acid with goes through the formation of a cocrystal of (S)-2-hydroxy-3-methoxy-3,3-diphenylpropanoic acid and a further compound selected from L-valine and L-2-aminobutyric acid. The process shows the following striking advantages: high yield and high ee (in one step, i.e. without the need of further crystallizations); low cost resolution agents; possibility to use a lower amount of resolution agent (0.5 to 0.25 eq.); easy to recover the resolution agent to be used for another resolution process; amino acids are easier to handle, less toxic and less prone to degradation than primary amines; use of low cost and safer solvents; and good filtration.

Consequently, this improved process has better industrial applicability and utility than the known processes and overcome the drawbacks of the existing ones. The identification of the right resolving agent is not a routine exercise and cannot be predicted theoretically. The state of the art does not give any indication as to the use of these resolution agents, nor about the formation of a cocrystal of (S)-2-hydroxy-3-methoxy-3,3-diphenylpropanoic acid and a further compound which is an amino acid, in particular, L-valine or L-2-aminobutyric acid.

According to our knowledge, the use of cocrystals for the preparation of Ambrisentan or Darusentan is also not known in the art.

Accordingly, an aspect of the present invention relates to the provision of a cocrystal of (S)-2-hydroxy-3-methoxy-3,3-diphenylpropanoic acid and an amino acid, in particular, L-valine or L-2-aminobutyric acid.

Another aspect of the present invention relates to a process for preparing a cocrystal of (S)-2-hydroxy-3-methoxy-3,3-diphenylpropanoic acid and an amino acid as a pure form or a mixture with (R)-2-hydroxy-3-methoxy-3,3-diphenylpropanoic acid comprising either (a) wet grinding of a mixture of 2-hydroxy-3-methoxy-3,3-diphenylpropanoic acid or (S)-2-hydroxy-3-methoxy-3,3-diphenylpropanoic acid and an amino acid in water, a $(C_1-C_4)$-alcohol, methyl isobutyl ketone, or ethyl acetate; and (b) isolating the compound thus obtained; or alternatively, (a') mixing 2-hydroxy-3-methoxy-3,3-diphenylpropanoic acid or (S)-2-hydroxy-3-methoxy-3,3-diphenylpropanoic acid and an amino acid in a mixture of $(C_1-C_4)$-alcohol/water at a temperature of from 40° C. to the reflux temperature of the solvent system used; (b') cooling the mixture; and (c') isolating the compound thus obtained.

The step (a') may be carried out by dissolving 2-hydroxy-3-methoxy-3,3-diphenylpropanoic acid and an amino acid in a mixture of $(C_1-C_4)$-alcohol/water. It can also be carried out by adding an aqueous solution of an amino acid over a solution of 2-hydroxy-3-methoxy-3,3-diphenylpropanoic acid in $(C_1-C_4)$-alcohol at a temperature of from 40 to 65° C. It can also be carried out by adding a solution of 2-hydroxy-3-methoxy-3,3-diphenylpropanoic acid in $(C_1-C_4)$-alcohol over an aqueous solution of an amino acid at a temperature of from 40 to 65° C.

Another aspect of the present invention relates to a process of resolution of 2-hydroxy-3-methoxy-3,3-diphenylpropanoic acid which comprises first preparing a cocrystal of (S)-2-hydroxy-3-methoxy-3,3-diphenylpropanoic acid and an amino acid by (a') mixing 2-hydroxy-3-methoxy-3,3-diphenylpropanoic acid and an amino acid in a mixture of $(C_1-C_4)$-alcohol/water at a temperature of from 40° C. to the reflux temperature of the solvent system used; (b') cooling the mixture; (c') isolating the compound thus obtained; and then dissociating the cocrystals thus obtained by mixing the cocrystal with a mixture of water and a solvent selected from $(C_2-C_6)$-ether and $(C_2-C_6)$-alkyl $(C_2-C_6)$-alkanoate, separating off the aqueous phase from the organic phase, optionally, carrying out extractions with the solvent used, and finally separating the (S)-2-hydroxy-3-methoxy-3,3-diphenylpropanoic acid from the joined organic phases. The (S)-2-hydroxy-3-methoxy-3,3-diphenylpropanoic acid may be separated by methods known in the art, for instance, crystallization or evaporation.

Another aspect of the present invention relates to another process of resolution of 2-hydroxy-3-methoxy-3,3-diphenylpropanoic acid which comprises first preparing a cocrystal (S)-2-hydroxy-3-methoxy-3,3-diphenylpropanoic acid and an amino acid by (a') mixing 2-hydroxy-3-methoxy-3,3-diphenylpropanoic acid and an amino acid in a mixture of $(C_1-C_4)$-alcohol/water at a temperature of from 40° C. to the reflux temperature of the solvent system used; (b') cooling the mixture; and (c') isolating the compound thus obtained; and then dissociating the cocrystals thus obtained by hot slurrying with an organic solvent selected from $(C_2-C_6)$-alkyl $(C_2-C_6)$-alkanoate, $(C_2-C_6)$-alcohol, and mixtures thereof, filtrating the amino acid, optionally washing the organic phase with water and separating the (S)-2-hydroxy-3-methoxy-3,3-diphenylpropanoic acid from the organic phase. The (S)-2-hydroxy-3-methoxy-3,3-diphenylpropanoic acid may be separated by methods known in the art, for instance, crystallization or evaporation.

The cocrystals of the invention may be purified by recrystallization or slurrying prior to their dissociation, for example, by recrystallization or by slurrying in an organic solvent or a mixture thereof, or in a mixture water/organic solvent.

Another aspect of the present invention is the use of the cocrystals of the present invention, that is, a cocrystal of (S)-2-hydroxy-3-methoxy-3,3-diphenylpropanoic acid and an amino acid for preparing Ambrisentan, Darusentan, or their pharmaceutically acceptable salts.

Finally, another aspect of the present invention relates to a process for preparing Ambrisentan, Darusentan, or their pharmaceutically acceptable salts which comprises carrying out any of the processes of resolution described above, and converting the (S)-2-hydroxy-3-methoxy-3,3-diphenylpropanoic acid thus obtained or a derivative thereof into Ambrisentan, Darusentan, or their salts by known processes in the art. It is also part of the invention the conversion of the cocrystals of the invention directly into Ambrisentan or Darusentan, without the need of isolation of the (S)-2-hydroxy-3-methoxy-3,3-diphenylpropanoic acid.

DETAILED DESCRIPTION OF THE INVENTION

Figure 1:
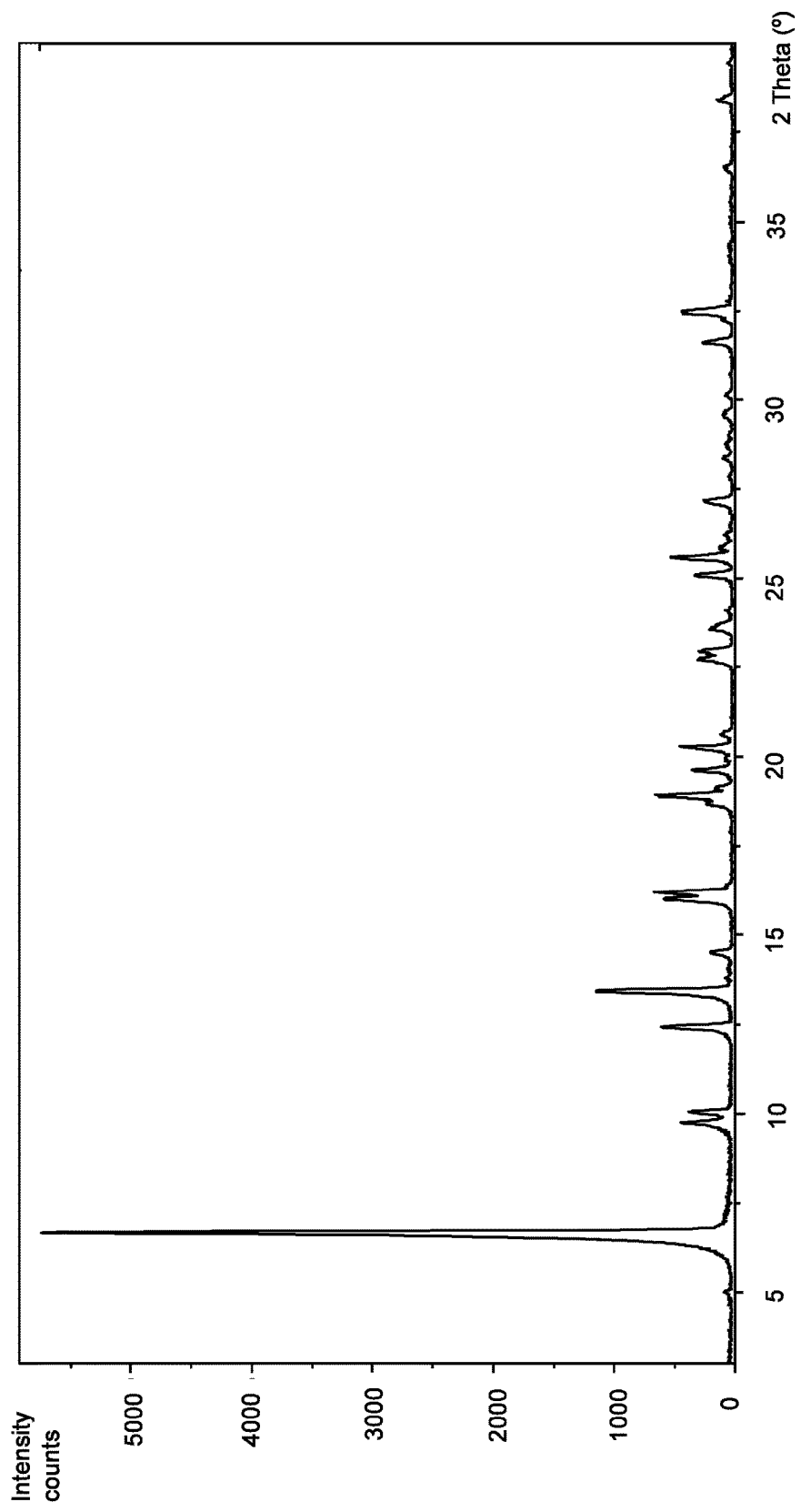
FIG. 1 shows the X-ray powder diffractogram (XRPD) of cocrystal (S)-2-hydroxy-3-methoxy-3,3-diphenylpropanoic acid-L-valine in a molar ratio 2:1, named Form I.

Definitions:

The term "cocrystal" refers herein to a crystalline entity with at least two different components constituting the unit cell at room temperature (20-25° C.) and interacting by weak interactions. Thus, in a cocrystal one component crystallizes with one or more neutral components. The cocrystals may include one or more solvent molecules in the crystal lattice.

The term "weak interaction" refers herein to an interaction which is neither ionic nor covalent, and includes for example: hydrogen bonds, van der Waals interactions, and π-π stacking.

The term "solvate" is to be understood as meaning any form of the cocrystal in which the compound has attached to it via non-covalent binding solvent molecules. When the solvent is water the solvate is a hydrate.

When a ratio of components of the cocrystals of the invention is specified it refers to the molar ratio between the components that forms the cocrystal.

The term "molar ratio" has been used to express the stoichiometric amount in mols of each of the components of a cocrystal.

When values of characteristic peaks of an X-ray diffractogram are given it is said that are "approximate" values. It should be understood that the values are the ones shown in the corresponding lists or tables ±0.1 degrees 2 theta measured in an X-ray diffractometer with Cu—K$_\alpha$ radiation λ=1.5406 Å.

The term "room temperature" as disclosed herein refers to a temperature of the environment, without heating or cooling, and is generally comprised of from 20 to 25° C.

The term "reflux temperature" as disclosed herein refers to the temperature where the mixture boils in circumstances such that the vapour returns to the stock of liquid after condensing.

The term "hot slurrying" as disclosed herein refers to stirring a suspension of a compound in an appropriate solvent at a temperature comprised of from 40° C. to 90° C., preferably at a temperature of about 80° C.

For the purposes of the invention, any ranges given include both the lower and the upper end-points of the range. Ranges given, such as temperatures, times, and the like, should be considered approximate, unless specifically stated.

The expression "cocrystal obtainable by" is used here to define each specific cocrystal of the invention by the process for obtaining it and refers to the product obtainable by any of the corresponding processes disclosed herein.

For the purposes of the invention the expressions "obtainable", "obtained" and equivalent expressions are used interchangeably, and in any case, the expression "obtainable" encompasses the expression "obtained".

The terms "wet grinding" and "liquid assisted grinding" are equivalent and refer to a technique which consists of milling or grinding the product or mixture with some drops of solvent added. Neat and liquid-assisted grinding are techniques that can be employed in order to produce cocrystals. In neat (dry) grinding, cocrystal formers are ground together manually using a mortar and pestle, using a ball mill, or using a vibratory mill. In liquid-assisted grinding, or kneading, a small or substoichiometric amount of liquid (solvent) is added to the grinding mixture.

As mentioned above it is part of the invention the provision of a cocrystal of (S)-2-hydroxy-3-methoxy-3,3-diphenylpropanoic acid and an amino acid. In a preferred embodiment, the amino acid is an α-amino acid.

In a more preferred embodiment, it is provided a cocrystal of (S)-2-hydroxy-3-methoxy-3,3-diphenylpropanoic acid and a compound selected from L-valine and L-2-aminobutyric acid.

The cocrystals of the invention may exist in solvated or unsolvated forms, including hydrated forms. It is to be understood that the invention encompasses all such solvated, as well as unsolvated forms. The obtention of solvates and hydrates depends on the solvent used and the crystallization conditions that can be determined by the skilled person.

The crystalline form of the cocrystals of the present invention has been characterized at least by X-ray powder diffraction (XRPD), proton nuclear magnetic resonance analyses $^1$H NMR (MeOD-d4), infrared spectroscopy (IR) and differential scanning calorimetry (DSC).

XRPD analyses were performed using a PANalytical X'Pert diffractometer with Cu—K$_\alpha$ radiation in Bragg-Brentano geometry. The system is equipped with a monodimensional, real time multiple strip detector. Diffractograms were recorded from 3° to 40° (2θ) at a scan rate of 17.6° per minute.

Proton nuclear magnetic resonance analyses were recorded in deuterated methanol (MeOD-d4) in a Varian Mercury 400 spectrometer, equipped with a broadband probe ATB 1H/19F/X of 5 mm. Spectra were acquired dissolving 5-10 mg of sample in 0.6 mL of deuterated solvent.

FTIR spectra were recorded using a Thermo Nicolet Nexus 870 FT-IR, equipped with a beamsplitter KBr system, a 35 mW He—Ne laser as the excitation source and a DTGS KBr detector. Spectra were acquired in 32 scans at a resolution of 4 cm$^{-1}$.

DSC analyses were recorded with a Mettler DSC822$^e$. Samples were weighed into a 40 μL aluminium crucible with a pinhole lid and were heated, under nitrogen (50 mL/min), at 10° C./min from 30 to 300° C.

Thermogravimetric analyses (TG) were recorded in a thermogravimetric analyzer Mettler TGA/SDTA851$^e$. Samples were weighed into a 70 μL alumina crucible with a pinhole lid and were heated at 10° C./min from 30 to 300° C., under nitrogen (50 mL/min).

In a particular embodiment, the cocrystal of (S)-2-hydroxy-3-methoxy-3,3-diphenylpropanoic acid and L-valine of the formula below is in a molar ratio 2:1, named herein cocrystal Form I.

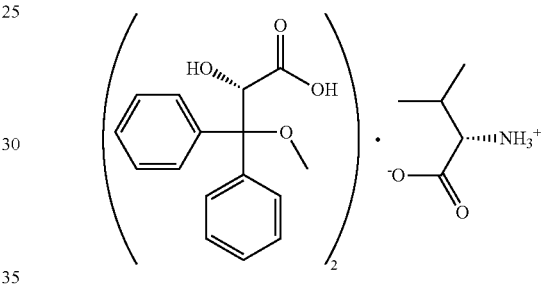

In a preferred embodiment, this cocrystal Form I is characterized by having an X-ray powder diffractogram that comprises characteristic peaks at approximately 6.7, 12.4, 13.5, 16.2 and 18.9 degrees 2 theta (Cu—K$_\alpha$ radiation, λ=1.5406 Å). In a more preferred embodiment, the cocrystal Form I is characterized by having an X-ray powder diffractogram that comprises further characteristic peaks at approximately 9.8, 16.0, 20.3, 25.6 and 32.5 degrees 2 theta (Cu—K$_\alpha$ radiation, λ=1.5406 Å).

More specifically, this new cocrystal Form I is characterized by exhibiting in the X-ray powder diffractogram a pattern of peaks, expressed in 2 theta units in degrees, 2θ (°), which is shown in Table 1.

TABLE 1

List of selected peaks (only peaks with relative intensity greater than or equal to 1% are indicated):

| Pos. [° 2Th.] | Rel. Int. [%] |
|---|---|
| 6.7 | 100 |
| 9.8 | 7 |
| 10.1 | 6 |
| 12.4 | 11 |
| 13.5 | 19 |
| 14.5 | 3 |
| 16.0 | 10 |
| 16.2 | 11 |
| 18.7 | 4 |
| 18.9 | 11 |
| 19.2 | 2 |
| 19.6 | 6 |

TABLE 1-continued

List of selected peaks (only peaks with relative intensity greater than or equal to 1% are indicated):

| Pos. [° 2Th.] | Rel. Int. [%] |
|---|---|
| 20.3 | 8 |
| 20.7 | 1 |
| 22.7 | 5 |
| 23.0 | 5 |
| 23.6 | 3 |
| 25.1 | 6 |
| 25.6 | 9 |
| 25.9 | 1 |
| 27.2 | 4 |
| 28.4 | 1 |
| 28.8 | 1 |
| 29.5 | 1 |
| 29.7 | 1 |
| 31.6 | 5 |
| 32.2 | 1 |
| 32.4 | 7 |
| 32.5 | 7 |
| 36.5 | 1 |
| 38.4 | 2 |

This cocrystal Form I may be further characterized by an X-ray diffractogram as in FIG. 1.

This cocrystal Form I may also be further characterized by the following $^1$H NMR spectrum (MeOD-d4, 400 MHz): δ=7.45-7.37 (m, 2×4H); 7.35-7.20 (m, 2×6H); 5.20 (s, 2×1H); 3.45 (d, J=4.3 Hz, 1H); 3.16 (s, 2×3H); 2.28 (dsept, J=4.3 Hz, J=7.0 Hz, 1H); 1.07 (d, J=7.0 Hz, 3H); 1.03 (d, J=7.0 Hz, 3H).

This cocrystal Form I may also be further characterized by the following IR (KBr): ν=3377 (s, br), 3197 (w), 2829 (w), 1725 (s), 985 (m), 889 (m), 756 (s), 697 (s) cm$^{-1}$.

This cocrystal Form I may also be further characterized in that the endothermic sharp peak corresponding to the melting point has an onset at 177.10° C. (fusion enthalpy −277.80 J/g), measured by DSC analysis (10° C./min).

This cocrystal Form I may also be further characterized by a TG analysis which shows no significant weight loss at temperatures lower than the melting point.

This cocrystal Form I is easy to handle and shows crystal stability at room temperature.

This cocrystal may be prepared as a pure form or as a mixture by a process comprising (a) wet grinding of a mixture of 2-hydroxy-3-methoxy-3,3-diphenylpropanoic acid or (S)-2-hydroxy-3-methoxy-3,3-diphenylpropanoic acid and L-valine in water, a ($C_1$-$C_4$)-alcohol such as methanol or isopropanol, methyl isobutyl ketone or ethyl acetate; and (b) isolating the compound thus obtained. In a preferred embodiment, the solvent is water. In another preferred embodiment, the solvent is methanol.

Preferably, this cocrystal is prepared by a process comprising (a') mixing 2-hydroxy-3-methoxy-3,3-diphenylpropanoic acid and L-valine in a mixture of ($C_1$-$C_4$)-alcohol/water at a temperature of from 40° C. to the reflux temperature of the solvent system used; (b') cooling the mixture; and (c') isolating the compound thus obtained. Preferably the ($C_1$-$C_4$)-alcohol is isopropanol. More preferably, a mixture of isopropanol/water 2:3 is used.

The step (a') may be carried out by dissolving 2-hydroxy-3-methoxy-3,3-diphenylpropanoic acid and L-valine in a mixture of ($C_1$-$C_4$)-alcohol/water. It can also be carried out by adding an aqueous solution of L-valine over a solution of 2-hydroxy-3-methoxy-3,3-diphenylpropanoic acid in ($C_1$-$C_4$)-alcohol at a temperature of from 40 to 65° C. It can also be carried out by adding a solution of 2-hydroxy-3-methoxy-3,3-diphenylpropanoic acid in ($C_1$-$C_4$)-alcohol over an aqueous solution of L-valine at a temperature of from 40 to 65° C.

In a particular embodiment, the mixture of step (a') is seeded to start the crystallization with the cocrystal Form I. The seeding cocrystal form may be obtained by any of the processes described above.

Generally, the molar ratio of 2-hydroxy-3-methoxy-3,3-diphenylpropanoic acid and L-valine starting materials of any of the previous processes is 2:1. A small excess of any of them could be used depending on the obtention process. Thus, the molar ratio can vary from 4:1 to 1:2, preferably 4:1 to 1:1.

The isolation step may include removing of the solvent, for example, by one or more of the following operations: filtration, filtration under vacuum, decantation, and centrifugation, or other suitable techniques as known to a skilled person in the art.

The compound isolated in any of the previous processes can be dried at room temperature, preferably under vacuum. Generally, the vacuum is comprised of 0.5 to 3 mbar.

The cocrystal of (S)-2-hydroxy-3-methoxy-3,3-diphenylpropanoic acid and L-valine Form I of the invention may also be defined by its preparation process. Accordingly, this aspect of the invention can be formulated as the cocrystal of (S)-2-hydroxy-3-methoxy-3,3-diphenylpropanoic acid and L-valine Form I as defined above, obtainable by any of the previous processes, optionally including any preferred or particular embodiment of the processes and possible combinations of some of the process features disclosed above.

In another particular embodiment, the cocrystal of (S)-2-hydroxy-3-methoxy-3,3-diphenylpropanoic acid and L-2-aminobutyric acid of the formula below is in a molar ratio 2:1, named herein cocrystal Form II.

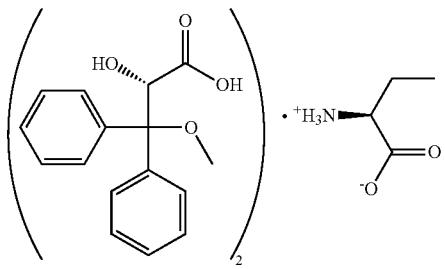

This cocrystal Form II is characterized by having an X-ray powder diffractogram that comprises characteristic peaks at approximately 6.6, 6.7, 10.0, 13.3 and 16.3 degrees 2 theta (Cu—K$_\alpha$ radiation, λ=1.5406 Å). In a still more preferred embodiment, the cocrystal Form II is characterized by having an X-ray powder diffractogram that comprises further characteristic peaks at approximately 10.3, 18.7, 20.1, 24.9 and 25.6 degrees 2 theta (Cu—K$_\alpha$ radiation, λ=1.5406 Å).

More specifically, this new cocrystal Form II is characterized by exhibiting in the X-ray powder diffractogram a pattern of peaks, expressed in 2 theta units in degrees, 2θ (°), which is shown in Table 2.

TABLE 2

List of selected peaks (only peaks with relative intensity greater than or equal to 1% are indicated):

| Pos. [° 2Th.] | Rel. Int. [%] |
|---|---|
| 5.1 | 3 |
| 6.6 | 100 |
| 6.7 | 92 |
| 9.8 | 11 |
| 10.0 | 15 |
| 10.3 | 14 |
| 12.3 | 10 |
| 13.3 | 28 |
| 13.5 | 11 |
| 14.2 | 3 |
| 14.4 | 6 |
| 16.1 | 13 |
| 16.3 | 21 |
| 18.5 | 6 |
| 18.7 | 11 |
| 19.2 | 3 |
| 19.4 | 3 |
| 19.7 | 2 |
| 20.0 | 8 |
| 20.1 | 11 |
| 20.8 | 4 |
| 22.5 | 5 |
| 22.7 | 5 |
| 23.0 | 2 |
| 23.9 | 3 |
| 24.4 | 1 |
| 24.9 | 11 |
| 25.6 | 12 |
| 26.4 | 2 |
| 26.8 | 1 |
| 27.3 | 2 |
| 29.2 | 3 |
| 30.2 | 2 |
| 30.4 | 2 |
| 31.4 | 3 |
| 32.1 | 6 |
| 32.4 | 5 |
| 37.2 | 1 |
| 38.2 | 2 |

Figure 2:
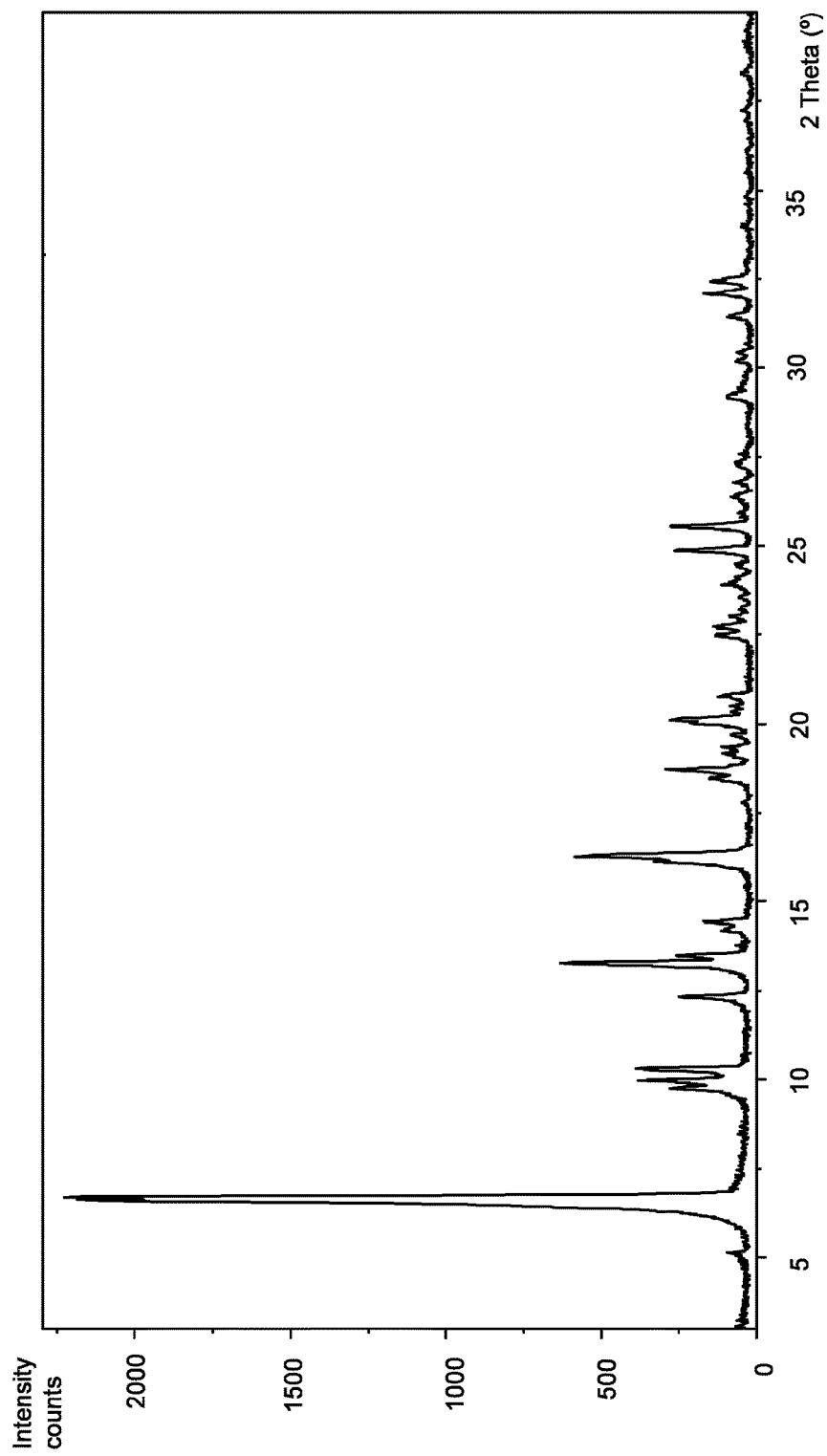
FIG. 2 shows the X-ray powder diffractogram (XRPD) of cocrystal (S)-2-hydroxy-3-methoxy-3,3-diphenylpropanoic acid-L-2-aminobutyric acid in a molar ratio 2:1, named Form II.

This cocrystal Form II may be further characterized by an X-ray diffractogram as in FIG. 2.

This cocrystal Form II may also be further characterized by the following $^1$H NMR spectrum (MeOD-d4, 400 MHz): δ=7.45-7.37 (m, 2×4H); 7.34-7.21 (m, 2×6H); 5.20 (s, 2×1H); 3.53 (dd, J=5.5 Hz, J=6.6 Hz, 1H); 3.16 (s, 2×3H); 1.97-1.79 (m, 2H); 1.03 (t, J=7.4 Hz, 3H).

This cocrystal Form II may also be further characterized by the following IR (KBr): ν=3372 (s, br), 3181 (w), 2828 (w), 1727 (s), 1632 (m), 982 (m), 841 (m), 757 (s), 635 (s) cm$^{-1}$.

This cocrystal Form II may also be further characterized in that the endothermic sharp peak corresponding to the melting point has an onset at 164.64° C. (fusion enthalpy −256.40 J/g), measured by DSC analysis (10° C./min).

This cocrystal Form II may also be further characterized by a TG analysis which shows no significant weight loss at temperatures lower than the melting point.

This cocrystal Form II is easy to handle and shows crystal stability at room temperature.

This cocrystal may be prepared as a pure form or as a mixture by a process comprising (a) wet grinding of a mixture of 2-hydroxy-3-methoxy-3,3-diphenylpropanoic acid or (S)-2-hydroxy-3-methoxy-3,3-diphenylpropanoic acid and L-2-aminobutyric acid in water, a (C$_1$-C$_4$)-alcohol such as methanol or isopropanol, methyl isobutyl ketone or ethyl acetate; and (b) isolating the compound thus obtained.

Preferably, this cocrystal is prepared by a process comprising (a') mixing 2-hydroxy-3-methoxy-3,3-diphenylpropanoic acid and L-2-aminobutyric acid in a mixture of (C$_1$-C$_4$)-alcohol/water at a temperature of from 40° C. to the reflux temperature of the solvent system used; (b') cooling the mixture; and (c') isolating the compound thus obtained. Preferably, the (C$_1$-C$_4$)-alcohol is isopropanol. More preferably, a mixture of isopropanol/water 2:3 is used.

The step (a') may be carried out by dissolving 2-hydroxy-3-methoxy-3,3-diphenylpropanoic acid and L-2-aminobutyric acid in a mixture of (C$_1$-C$_4$)-alcohol/water. It can also be carried out by adding an aqueous solution of L-2-aminobutyric acid over a solution of 2-hydroxy-3-methoxy-3,3-diphenylpropanoic acid in (C$_1$-C$_4$)-alcohol at a temperature of from 40 to 65° C. It can also be carried out by adding a solution of 2-hydroxy-3-methoxy-3,3-diphenylpropanoic acid in (C$_1$-C$_4$)-alcohol over an aqueous solution of L-2-aminobutyric acid at a temperature of from 40 to 65° C.

In a particular embodiment, the mixture of step (a') is seeded to start the crystallization with the cocrystal Form II. The seeding cocrystal form may be obtained by any of the processes described above.

Generally, the molar ratio of 2-hydroxy-3-methoxy-3,3-diphenylpropanoic acid and L-2-aminobutyric acid starting materials of any of the previous processes is 2:1. A small excess of any of them could be used depending on the obtention process. Thus, the molar ratio can vary from 4:1 to 1:2, preferably 4:1 to 1:1.

The isolation step may include removing of the solvent, for example, by one or more of the following operations: filtration, filtration under vacuum, decantation, and centrifugation, or other suitable techniques as known to a skilled person in the art.

The compound isolated in any of the previous processes can be dried at room temperature, preferably under vacuum. Generally, the vacuum is comprised of 0.5 to 3 mbar.

The cocrystal of (S)-2-hydroxy-3-methoxy-3,3-diphenylpropanoic acid and L-2-aminobutyric acid Form II of the invention may also be defined by its preparation process. Accordingly, this aspect of the invention can be formulated as the cocrystal of (S)-2-hydroxy-3-methoxy-3,3-diphenylpropanoic acid and L-2-aminobutyric acid Form II as defined above, obtainable by any of the previous processes, optionally including any preferred or particular embodiment of the processes and possible combinations of some of the process features disclosed above.

The cocrystals of (S)-2-hydroxy-3-methoxy-3,3-diphenylpropanoic acid and a compound selected from L-valine and L-2-aminobutyric acid may be easily converted into the (S)-2-hydroxy-3-methoxy-3,3-diphenylpropanoic acid in high yield.

Thus, it is also part of the invention a process of resolution of 2-hydroxy-3-methoxy-3,3-diphenylpropanoic acid which comprises: first, preparing a cocrystal of (S)-2-hydroxy-3-methoxy-3,3-diphenylpropanoic acid and a compound selected from the group consisting of L-valine and L-2-aminobutyric acid by (a') mixing 2-hydroxy-3-methoxy-3,3-diphenylpropanoic acid and a compound selected from the group consisting of L-valine and L-2-aminobutyric acid in a mixture of (C$_1$-C$_4$)-alcohol/water, at a temperature of from 40° C. to the reflux temperature of the solvent system used, preferably, isopropanol/water; (b') cooling the mixture and (c') isolating the compound thus obtained; and subsequently, (d') dissociating the cocrystals previously obtained by mixing the cocrystal with a mixture of water and a solvent selected from a (C$_2$-C$_6$)-ether such as methyl tert-butyl ether, and (C$_2$-C$_6$)-alkyl (C$_2$-C$_6$)-alkanoate such as ethyl acetate, separating off the aqueous phase from the organic phase, optionally, carrying out extractions with the solvent used, and finally separating the (S)-2-hydroxy-3-methoxy-3,3-diphenylpropanoic acid from the joined organic phases. Preferably, the solvent used is tert-butylmethyl ether.

Removing of the solvent may include, for example, one or more of the following operations: filtration, filtration under vacuum, evaporation, decantation, centrifugation and other suitable techniques as known to a skilled person in the art.

It is also part of the invention a process of resolution of 2-hydroxy-3-methoxy-3,3-diphenylpropanoic acid which comprises: first preparing a cocrystal of (S)-2-hydroxy-3-methoxy-3,3-diphenylpropanoic acid and a compound selected from the group consisting of L-valine and L-2-aminobutyric acid by (a') mixing 2-hydroxy-3-methoxy-3,3-diphenylpropanoic acid and a compound selected from the group consisting of L-valine and L-2-aminobutyric acid in a mixture of ($C_1$-$C_4$)-alcohol/water at a temperature of from 40° C. to the reflux temperature of the solvent system used, preferably isopropanol/water (b') cooling the mixture; and (c') isolating the compound thus obtained; and then dissociating the cocrystals thus obtained by hot slurrying with an organic solvent selected from the group consisting of ($C_2$-$C_6$)-alkyl ($C_2$-$C_6$)-alkanoate or ($C_2$-$C_6$)-alcohol, and mixtures thereof; filtrating the amino acid; optionally washing the organic phase with water; and separating the (S)-2-hydroxy-3-methoxy-3,3-diphenylpropanoic acid from the organic phase. Preferably, the organic solvent is ethyl acetate or isopropanol. Removing of the solvent may include, for example, one or more of the following operations: filtration, filtration under vacuum, evaporation, decantation, and centrifugation and other suitable techniques as known to a skilled person in the art.

The cocrystals of the invention may also be purified by recrystallization or by slurrying prior to their dissociation and subsequent condensation of the compound obtained with 4,6-dimethyl-2-(methylsulfonyl)pyrimidine or with 4,6-dimethoxy-2-(methylsulfonyl)pyrimidine. Thus, in a particular embodiment, an additional step of purification is carried out to reach the desired optical purity of the cocrystals of the present invention, as for example, by recrystallization or by slurrying in an organic solvent or a mixture thereof, or in a mixture water/organic solvent. Preferably, the slurrying is carried out at room temperature. Preferably, the solvents used in both processes are the same used for the preparation of the cocrystal. For instance, the organic solvent may be a ($C_1$-$C_4$)-alcohol or mixtures thereof or their mixture with water. More preferably, the mixture is a mixture of isopropanol/water. Depending on the amount of solvents and the temperature it is carried out the recrystallization or the slurrying.

It is part of the invention any process for preparing Ambrisentan, Darusentan or a salt thereof, comprising carrying out the preparation processes of the cocrystals of the invention defined above.

It is also part of the invention any process for preparing Ambrisentan, Darusentan or a salt thereof, comprising carrying out the resolution of 2-hydroxy-3-methoxy-3,3-diphenylpropanoic acid as defined above comprising the preparation of the cocrystals of the invention and the dissociation step.

In a particular embodiment, the process for preparing Ambrisentan, Darusentan or a salt thereof comprises first preparing the cocrystals of the invention by the process defined above, and then the following further steps:

(i) either reacting the cocrystals of the invention as obtained above with 4,6-dimethyl-2-(methylsulfonyl)pyrimidine in the presence of an inert solvent system and a base to yield Ambrisentan, or with 4,6-dimethoxy-2-(methylsulfonyl)pyrimidine in the presence of an inert solvent system and a base to yield Darusentan, or alternatively, (i') first dissociating the cocrystals of the invention by any of the processes disclosed above, and then reacting the (S)-2-hydroxy-3-methoxy-3,3-diphenylpropanoic acid obtained with 4,6-dimethyl-2-(methylsulfonyl)pyrimidine in the presence of an inert solvent system and a base to yield Ambrisentan, or with 4,6-dimethoxy-2-(methylsulfonyl)pyrimidine in the presence of an inert solvent system and a base to yield Darusentan, or alternatively, (i'') first dissociating the cocrystals of the invention by any of the processes disclosed above, followed by preparing a derivative of (S)-2-hydroxy-3-methoxy-3,3-diphenylpropanoic acid, and then reacting the derivative of (S)-2-hydroxy-3-methoxy-3,3-diphenylpropanoic acid with 4,6-dimethyl-2-(methylsulfonyl)pyrimidine in the presence of an inert solvent system and a base, followed by hydrolyzing the compound thus obtained to yield Ambrisentan; or with 4,6-dimethoxy-2-(methylsulfonyl)pyrimidine in the presence of an inert solvent system and a base, followed by hydrolyzing the compound thus obtained to yield Darusentan and (ii) optionally, converting the compound obtained in step (i), (i'), or (i'') into a pharmaceutically acceptable salt by reacting the free acid with a pharmaceutically acceptable base.

In another particular embodiment of the invention, the process for preparing Ambrisentan or its salts comprises providing a cocrystal of (S)-2-hydroxy-3-methoxy-3,3-diphenylpropanoic acid and an amino acid; and then carrying out the steps (i), or alternatively (i'), or alternatively (i'') and (ii) as defined above.

Suitable bases which can be used for the above couplings with the 4,6-dimethyl-2-(methylsulfonyl)pyrimidine or with the 4,6-dimethoxy-2-(methylsulfonyl)pyrimidine may include a metal hydroxide such as sodium or potassium hydroxide, a metal carbonate such as sodium or potassium carbonate, a metal bicarbonate such as sodium or potassium bicarbonate, a metal alkoxide such as sodium or potassium tert-butoxide, sodium hydride, or alkali metal amides such as lithium diisopropylamide or lithium amide.

Suitable solvents include dimethylsulfoxide, N,N-dimethylformamide; acetonitrile, acetone, diethyl ether or tetrahydrofurane. Preferably, the temperature ranges from room temperature to the boiling point of the solvent employed.

As explained above in detail, the dissociation step of the cocrystals may be carried out by mixing the cocrystal with a mixture of water and a solvent selected from a ($C_2$-$C_6$)-ether such as methyl tert-butyl ether, and ($C_2$-$C_6$)-alkyl ($C_2$-$C_6$)-alkanoate such as ethyl acetate, separating off the aqueous phase from the organic phase, optionally, carrying out extractions with the solvent used, and finally separating the (S)-2-hydroxy-3-methoxy-3,3-diphenylpropanoic acid from the joined organic phases, or by hot slurrying with an organic solvent selected from the group consisting of ($C_2$-$C_6$)-alkyl ($C_2$-$C_6$)-alkanoate or ($C_2$-$C_6$)-alcohol, and mixtures thereof; filtrating the amino acid; optionally washing the organic phase with water; and separating the (S)-2-hydroxy-3-methoxy-3,3-diphenylpropanoic acid from the organic phase.

When a derivative of (S)-2-hydroxy-3-methoxy-3,3-diphenylpropanoic acid is used, the process further comprises a previous step of preparing the derivative of (S)-2-hydroxy-3-methoxy-3,3-diphenylpropanoic acid which is an ester such as methyl ester, by reacting the (S)-2-hydroxy-3- methoxy-3,3-diphenylpropanoic acid with an esterifying agent. In addition, in this embodiment, after the alkylation of the compound thus obtained with 4,6-dimethyl-2-(methylsulfonyl)pyrimidine, the process further comprises a further step of hydrolyzing the compound obtained to yield Ambrisentan. The hydrolysis may be carried out using a suitable base, for instance, a metal hydroxide such as sodium or potassium hydroxide, or a metal carbonate such as sodium or potassium carbonate, in a suitable solvent, for instance N,N-dimethylformamide or a ($C_2$-$C_6$)-ether.

When the alkylation step is carried out directly from the cocrystals of the invention, after reacting the cocrystal with a suitable base, for instance with lithium amide, to form the corresponding salt of (S)-2-hydroxy-3-methoxy-3,3-diphenylpropanoic acid it may be reacted with 4,6-dimethyl-2-(methylsulfonyl)pyrimidine. The reaction is carried out in the presence of a suitable base from those mentioned above and a suitable solvent from those mentioned above.

The term "pharmaceutically acceptable salts" used herein encompasses any salt formed from pharmaceutically acceptable non-toxic bases including inorganic or organic bases. There is no limitation regarding the salts, except that if used for therapeutic purposes, they must be pharmaceutically acceptable.

The preparation of pharmaceutically acceptable salts of Ambrisentan or Darusentan can be carried out by methods known in the art. For instance, they can be prepared from Ambrisentan, which contains an acidic moiety, by conventional chemical methods. Generally, such salts are prepared by reacting the free acid of Ambrisentan or of Darusentan with a stoichiometric amount of the appropriate pharmaceutically acceptable base in water or in an organic solvent or in a mixture of them. Examples of appropriate organic solvents include ($C_1$-$C_6$)-alcohols or ethyl acetate.

It is also part of the present invention the provision of a single reaction step of the process to obtain (S)-2-hydroxy-3-methoxy-3,3-diphenylpropanoic acid, as well as the combination of two or more sequential steps of the process. Likewise, it is also part of the present invention the provision of a single reaction step of the process of preparing Ambrisentan or Darusentan directly from the cocrystals of the invention, as well as the combination of two or more sequential steps of this process, with the proviso that these reaction steps comprise the step in which is used one of the cocrystals of the invention as starting material.

With regard to the specific conditions for carrying out the process of the invention, the skilled person would know how to adjust the parameters of each of the steps indicated above in the light of the description and examples of the present invention.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Example 1

Preparation of the cocrystal of (S)-2-hydroxy-3-methoxy-3,3-diphenylpropanoic acid-L-valine (2:1) (Form I) by wet grinding in water and without seeding To a 2 mL eppendorf containing 2-hydroxy-3-methoxy-3,3-diphenylpropanoic acid (35 mg, 0.13 mmol), L-valine (15 mg, 0.13 mmol) and three 4 mm stainless steel grinding balls, one drop of water was added. The reactor was stirred 45 minutes at a rate of 30 Hz (3×15 minutes). The product was dried under vacuum at room temperature. A mixture of (S)-2-hydroxy-3-methoxy-3,3-diphenylpropanoic acid-L-valine (2:1) (Form I), (R)-2-hydroxy-3-methoxy-3,3-diphenylpropanoic acid and L-valine was obtained as a white powder. According to XRPD, the compound of the title is present in the mixture.

The same experiment was carried out with MeOH instead of water with the same result.

Example 2

Resolution by preparing the cocrystal of (S)-2-hydroxy-3-methoxy-3,3-diphenylpropanoic acid-L-valine (2:1) (Form I) by crystallization in water/IPA (3:2) without seeding To an assay tube equipped with magnetic stirrer containing 2-hydroxy-3-methoxy-3,3-diphenylpropanoic acid (41 mg, 0.15 mmol) and L-valine (9 mg, 0.08 mmol) was added a mixture of water/IPA (3:2) (0.5 mL). The resulting suspension was heated at reflux until complete dissolution and then cooled down to room temperature. A white precipitate was formed and the slurry was stirred at room temperature for 4 hours. The solid was filtered with a sintered funnel (porosity 4), washed with water/IPA (3:2) (0.15 mL) and dried under vacuum at room temperature. (S)-2-hydroxy-3-methoxy-3,3-diphenylpropanoic acid-L-valine (2:1) (Form I) was obtained as a white powder (18 mg, 36% yield, 89% ee). According to $^1$H NMR (MeOD-d4, 400 MHz) and XRPD it corresponds to the compound of the title.

Example 3

Resolution by preparing the cocrystal of (S)-2-hydroxy-3-methoxy-3,3-diphenylpropanoic acid-L-valine (2:1) (Form I) by crystallization in water/IPA (3:2) with 0.5 eq. of L-valine with seeding To a round-bottom flask equipped with magnetic stirrer containing 2-hydroxy-3-methoxy-3,3-diphenylpropanoic acid (1.65 g, 6.06 mmol) and L-valine (0.35 g, 2.99 mmol, 0.5 eq.) was added a mixture of water/IPA (3:2) (16 mL). The resulting suspension was heated at 100° C. (bath temperature) until complete dissolution and then cooled down to room temperature. The solution was seeded with Form I, obtained in Example 2, at 60-70° C. A white precipitate was formed and the slurry was stirred at room temperature for 2 hours. The solid was filtered with a sintered funnel (porosity 3), washed with water/IPA (3:2) (2×4 mL) and dried under vacuum at room temperature. (S)-2-hydroxy-3-methoxy-3,3-diphenylpropanoic acid-L-valine (2:1) (Form I) was obtained as a white powder (0.79 g, 40% yield, 99% ee).

According to ¹H NMR (MeOD-d4, 400 MHz) and XRPD it corresponds to the compound of the title.

Example 4

Resolution by preparing the cocrystal of (S)-2-hydroxy-3-methoxy-3,3-diphenylpropanoic acid-L-valine (2:1) (Form I) by crystallization in water/IPA (3:2) with 0.26 eq. of L-valine with seeding To an assay tube equipped with magnetic stirrer containing 2-hydroxy-3-methoxy-3,3-diphenylpropanoic acid (181 mg, 0.66 mmol) and L-valine (20 mg, 0.17 mmol, 0.26 eq.) was added a mixture of water/IPA (3:2) (1.6 mL). The resulting suspension was heated at reflux until complete dissolution and then cooled down to room temperature. The solution was seeded with Form I, obtained in Example 2, at 60° C. A white precipitate was formed and the slurry was stirred at room temperature for 2 hours. The solid was filtered with a sintered funnel (porosity 4), washed with water/IPA (3:2) (2×0.5 mL) and dried under vacuum at room temperature. (S)-2-hydroxy-3-methoxy-3,3-diphenylpropanoic acid-L-valine (2:1) (Form I) was obtained as a white powder (74 mg, 34% yield, 96% ee). According to ¹H NMR (MeOD-d4, 400 MHz) and XRPD it corresponds to the compound of the title.

Example 5

Preparation of (S)-2-hydroxy-3-methoxy-3,3-diphenylpropanoic acid by dissociation of cocrystal of (S)-2-hydroxy-3-methoxy-3,3-diphenylpropanoic acid-L-valine (2:1) (Form I) in water/TBME and extraction of the compound obtained in TBME To a round-bottom flask equipped with magnetic stirrer containing Form I (98% ee) (200 mg, 0.30 mmol) was added a mixture of water/TBME (1:1) (10 mL). The resulting mixture was stirred at room temperature for 30 minutes. After phase separation, the aqueous phase was separated off and extracted with TBME (3×5 mL). The combined organic extracts were washed with water (10 mL), dried (MgSO$_4$) and distilled under vacuum to yield (S)-2-hydroxy-3-methoxy-3,3-diphenylpropanoic acid as a white solid (157 mg, 95% yield, 99% ee).

Example 6

Preparation of (S)-2-hydroxy-3-methoxy-3,3-diphenylpropanoic acid by dissociation of cocrystal of (S)-2-hydroxy-3-methoxy-3,3-diphenylpropanoic acid-L-valine (2:1) (Form I) in AcOEt To an assay tube equipped with magnetic stirrer containing Form I (97.5% ee) (180 mg, 0.27 mmol) was added AcOEt (3.6 mL). The resulting suspension was stirred at 80° C. (bath temperature) for 3 hours. The solid was filtered with a sintered funnel (porosity 4), washed with hot AcOEt (1 mL) and dried under vacuum at room temperature. L-valine was obtained as a white powder (31 mg, 97% yield). The filtrate was washed with water (1.5 mL), dried (MgSO$_4$) and distilled under vacuum to yield (S)-2-hydroxy-3-methoxy-3,3-diphenylpropanoic acid as a white solid (quantitative yield, 97% ee)

Example 7

Preparation of (S)-2-hydroxy-3-methoxy-3,3-diphenylpropanoic acid by dissociation of cocrystal of (S)-2-hydroxy-3-methoxy-3,3-diphenylpropanoic acid-L-valine (2:1) (Form I) in IPA To an assay tube equipped with magnetic stirrer containing Form 1 (97% ee) (50 mg, 0.08 mmol) was added IPA (1 mL). The resulting suspension was stirred at 80° C. (bath temperature) for 3 hours. The solid was filtered with a sintered funnel (porosity 4), washed with hot IPA (0.5 mL) and dried under vacuum at room temperature. L-valine was obtained as a white powder (7.2 mg, 81% yield). The filtrate was distilled under vacuum to yield (S)-2-hydroxy-3-methoxy-3,3-diphenylpropanoic acid as a white solid (40 mg, 98% yield, 97% ee)

Example 8

Preparation of the cocrystal of (S)-2-hydroxy-3-methoxy-3,3-diphenylpropanoic acid-L-2-aminobutyric acid (2:1) (Form II) by wet grinding in water without seeding To a 2 mL eppendorf containing 2-hydroxy-3-methoxy-3,3-diphenylpropanoic acid (25 mg, 0.09 mmol), L-2-aminobutyric acid (10 mg, 0.10 mmol) and three 4 mm stainless steel grinding balls, one drop of water was added. The reactor was stirred 45 minutes at a rate of 30 Hz (3×15 minutes). The product was dried under vacuum at room temperature. A mixture of (S)-2-hydroxy-3-methoxy-3,3-diphenylpropanoic acid-L-2-aminobutyric acid (2:1) (Form II), (R)-2-hydroxy-3-methoxy-3,3-diphenylpropanoic acid and L-2-aminobutyric acid was obtained as a white powder. According to XRPD the compound of the title is present in the mixture.

The same experiment was carried out with IPA, AcOEt or methyl isobutyl ketone with the same result.

Example 9

Resolution by preparing the cocrystal of (S)-2-hydroxy-3-methoxy-3,3-diphenylpropanoic acid-L2-aminobutyric acid (2:1) (Form II) by crystallization in Water/IPA (3:2)

To a round-bottom flask equipped with magnetic stirrer containing 2-hydroxy-3-methoxy-3,3-diphenylpropanoic acid (420 mg, 1.54 mmol) and L-2-aminobutyric acid (80 mg, 0.78 mmol) was added a mixture of water/IPA (3:2) (4 mL). The resulting suspension was heated at 60° C. (bath temperature) until complete dissolution and then cooled down to room temperature. The solution was seeded with Form II at 40° C. A white precipitate was formed and the slurry was stirred at room temperature for 2 hours. The solid was filtered with a sintered funnel (porosity 3), washed with water/IPA (3:2) (2×1 mL) and dried under vacuum at room temperature. (S)-2-hydroxy-3-methoxy-3,3-diphenylpropanoic acid-L2-aminobutyric acid (2:1) (Form II) was obtained as a white powder (138 mg, 28% yield, 97% ee).

REFERENCES CITED IN THE APPLICATION

U.S. Pat. No. 5,932,730
U.S. Pat. No. 6,559,338
WO2012017441A1

WO2011004402A2
WO2010070658A2
*Organic Process Research & Development*, 2001, vol. 5, pp. 16-22

The invention claimed is:

1. A cocrystal of (S)-2-hydroxy-3-methoxy-3,3-diphenylpropanoic acid and an amino acid; wherein the amino acid is selected from the group consisting of L-valine and L-2-aminobutyric acid, wherein the cocrystal is
   a cocrystal of (S)-2-hydroxy-3-methoxy-3,3-diphenylpropanoic acid-L-valine in a molar ratio 2:1, which is characterized by having an X-ray powder diffractogram that comprises characteristic peaks at approximately 6.7, 12.4, 13.5, 16.2 and 18.9 degrees 2 theta at a Cu—$K_\alpha$ radiation, $\lambda$=1.5406 Å; or
   a cocrystal(S)-2-hydroxy-3-methoxy-3,3-diphenylpropanoic acid-L-2-aminobutyric acid in a molar ratio 2:1, which is characterized by having an X-ray powder diffractogram that comprises characteristic peaks at approximately 6.6, 6.7, 10.0, 13.3 and 16.3 degrees 2 theta at a Cu—$K_\alpha$ radiation, $\lambda$=1.5406 Å.

2. The cocrystal according to claim 1, which is a cocrystal of (S)-2-hydroxy-3-methoxy-3,3-diphenylpropanoic acid-L-valine in a molar ratio 2:1, which is characterized by having an X-ray powder diffractogram that comprises characteristic peaks at approximately 6.7, 12.4, 13.5, 16.2 and 18.9 degrees 2 theta at a Cu—$K_\alpha$ radiation, $\lambda$=1.5406 Å.

3. The cocrystal according to claim 1, which is a cocrystal (S)-2-hydroxy-3-methoxy-3,3-diphenylpropanoic acid-L-2-aminobutyric acid in a molar ratio 2:1, which is characterized by having an X-ray powder diffractogram that comprises characteristic peaks at approximately 6.6, 6.7, 10.0, 13.3 and 16.3 degrees 2 theta at a Cu—$K_\alpha$ radiation, $\lambda$=1.5406 Å.

4. A process for preparing a cocrystal of (S)-2-hydroxy-3-methoxy-3,3-diphenylpropanoic acid and an amino acid as defined in claim 1, comprising (a') mixing 2-hydroxy-3-methoxy-3,3-diphenylpropanoic acid and an amino acid selected from the group consisting of L-valine and L-2-aminobutyric acid in a mixture of ($C_1$-$C_4$)-alcohol/water at a temperature of from 40° C. to the reflux temperature of the solvent system used;
   (b') cooling the mixture and
   (c') isolating the compound thus obtained.

5. The process according to claim 4, further comprising an additional step of purifying the cocrystal obtained by recrystallization or by slurrying in an organic solvent, a mixture thereof or a mixture of water/organic solvent.

6. The process according to claim 4, further comprising dissociating the cocrystals obtained in claim 4, either
   by mixing the cocrystal with a mixture of water and a solvent selected from a ($C_2$-$C_6$)-ether, and ($C_2$-$C_6$)-alkyl ($C_2$-$C_6$)-alkanoate; separating off the aqueous phase from the organic phase; optionally, carrying out extractions with the solvent used; and finally separating the (S)-2-hydroxy-3-methoxy-3,3-diphenylpropanoic acid from the joined organic phases; or alternatively,
   by hot slurrying with an organic solvent selected from ($C_2$-$C_6$)-alkyl ($C_2$-$C_6$)-alkanoate, ($C_2$-$C_6$)-alcohol, and mixtures thereof; filtrating the amino acid; optionally washing the organic phase with water; and finally separating the (S)-2-hydroxy-3-methoxy-3,3-diphenylpropanoic acid from the organic phase.

7. A process for preparing Ambrisentan or a salt thereof, comprising carrying out the process of claim 4, and then the following further steps:
   (i) reacting the cocrystals thus obtained with 4,6-dimethyl-2-(methylsulfonyl)pyrimidine in the presence of an inert solvent system and a base to yield Ambrisentan; and
   (ii) optionally, converting the compound obtained in step (i) into a pharmaceutically acceptable salt by reacting the free acid with a pharmaceutically acceptable base.

8. The process according to claim 5, further comprising dissociating the cocrystals obtained in claim 5, either
   by mixing the cocrystal with a mixture of water and a solvent selected from a ($C_2$-$C_6$)-ether, and ($C_2$-$C_6$)-alkyl ($C_2$-$C_6$)-alkanoate; separating off the aqueous phase from the organic phase; optionally, carrying out extractions with the solvent used; and finally separating the (S)-2-hydroxy-3-methoxy-3,3-diphenylpropanoic acid from the joined organic phases; or alternatively,
   by hot slurrying with an organic solvent selected from ($C_2$-$C_6$)-alkyl ($C_2$-$C_6$)-alkanoate, ($C_2$-$C_6$)-alcohol, and mixtures thereof; filtrating the amino acid; optionally washing the organic phase with water; and finally separating the (S)-2-hydroxy-3-methoxy-3,3-diphenylpropanoic acid from the organic phase.

9. A process for preparing Ambrisentan or a salt thereof, comprising carrying out the process of claim 6, and then the following further steps:
   (i') reacting the (S)-2-hydroxy-3-methoxy-3,3-diphenylpropanoic acid obtained with 4,6-dimethyl-2-(methylsulfonyl)pyrimidine in the presence of an inert solvent system and a base to yield Ambrisentan; or alternatively,
   (i") preparing a derivative of (S)-2-hydroxy-3-methoxy-3,3-diphenylpropanoic acid, and then reacting the derivative of (S)-2-hydroxy-3-methoxy-3,3-diphenylpropanoic acid with 4,6-dimethyl-2-(methylsulfonyl)pyrimidine in the presence of an inert solvent system and a base, followed by hydrolyzing the compound thus obtained to yield Ambrisentan;
   and
   (ii) optionally, converting the compound obtained in step (i') or (i") into a pharmaceutically acceptable salt by reacting the free acid with a pharmaceutically acceptable base.

10. A process for preparing Darusentan or a salt thereof, comprising carrying out the process of claim 4, and then the following further steps:
   (i) reacting the cocrystals thus obtained with 4,6-dimethoxy-2-(methylsulfonyl)pyrimidine in the presence of an inert solvent system and a base to yield Darusentan, and
   (ii) optionally, converting the compound obtained in step (i) into a pharmaceutically acceptable salt by reacting the free acid with a pharmaceutically acceptable base.

11. A process for preparing Darusentan or a salt thereof, comprising carrying out the process of claim 6, and then the following further steps:
   (i') reacting the (S)-2-hydroxy-3-methoxy-3,3-diphenylpropanoic acid obtained with 4,6-dimethoxy-2-(methylsulfonyl)pyrimidine in the presence of an inert solvent system and a base to yield Darusentan; or alternatively,
   (i") preparing a derivative of (S)-2-hydroxy-3-methoxy-3,3-diphenylpropanoic acid, and then reacting the derivative of (S)-2-hydroxy-3-methoxy-3,3-diphenylpropanoic acid with 4,6-dimethoxy-2-(methylsulfonyl)pyrimidine in the presence of an inert solvent system and a base, followed by hydrolyzing the compound thus obtained to yield Darusentan;

and (ii) optionally, converting the compound obtained in step (i') or (i") into a pharmaceutically acceptable salt by reacting the free acid with a pharmaceutically acceptable base.

* * * * *